United States Patent [19]

Kanda et al.

[11] Patent Number: 5,021,423
[45] Date of Patent: Jun. 4, 1991

[54] MITOMYCIN DERIVATIVES AND INTERMEDIATES THEREFOR

[75] Inventors: Yutaka Kanda, Houston, Tex.; Hitoshi Arai, Shizuoka, Japan; Masaji Kasai, Kanagawa, Japan; Makoto Morimoto, Shizuoka, Japan

[73] Assignee: Kyowa Hakko Kogyo Kabushiki Kaisha, Japan

[21] Appl. No.: 358,272

[22] Filed: May 26, 1989

[30] Foreign Application Priority Data

May 30, 1988 [JP] Japan .............................. 63-131914
Mar. 10, 1989 [JP] Japan .................................. 1-58278

[51] Int. Cl.⁵ .................... C07D 492/22; A61K 31/40
[52] U.S. Cl. .................................. 514/262; 548/407; 548/422
[58] Field of Search ................. 548/422, 407, 408; 514/262

[56] References Cited

U.S. PATENT DOCUMENTS

| | | | |
|---|---|---|---|
| 4,264,504 | 4/1981 | Urakawa et al. | 260/326.5 |
| 4,374,774 | 2/1983 | Kasai et al. | 548/422 |
| 4,395,558 | 7/1983 | Kasai et al. | 548/422 |
| 4,791,113 | 12/1988 | Kunda et al. | 548/422 |
| 4,814,445 | 3/1989 | Vyas et al. | 548/422 |
| 4,880,825 | 11/1989 | Kasai et al. | 548/407 |

FOREIGN PATENT DOCUMENTS 0344990 12/1989 European Pat. Off. .
122797 9/1979 Japan .
45322 3/1980 Japan .
118396 9/1980 Japan .

OTHER PUBLICATIONS

The Merck Index, 10th Edition, 890-891 and 1097 (1983).

*Primary Examiner*—Nicholas S. Rizzo
*Attorney, Agent, or Firm*—Schweitzer, Cornman & Gross

[57] ABSTRACT

Mitomycin derivatives having the formula

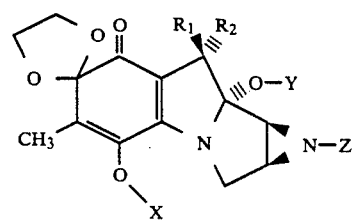

wherein
  X is acyl, lower alkyl, alkoxycarbonyl aryloxycarbonyl or aralkoxycarbonyl;
  Y is hydrogen or methyl;
  Z is hydrogen, methyl, acyl or allyloxycarbonyl;
  one of $R_1$ and $R_2$ represents carbamoyloxymethyl and the other represents hydrogen, or $R_1$ and $R_2$ together represent methylene, show antibacterial and antitumor activities.

9 Claims, No Drawings

MITOMYCIN DERIVATIVES AND INTERMEDIATES THEREFOR

The present invention relates to novel mitomycin derivatives having anti-bacterial and anti-tumor activities, and to intermediates therefor.

Mitomycins, in general, are known antibiotics having anti-bacterial and anti-tumour activities. Mitomycins originating from naturally-occurring substances are typically exemplified by mitomycin C, and mitomycins found only in trace amounts such as mitomycin A, mitomycin B and porfiromycin [cf Merck Index, 10th Edition]. Further examples of characterized mitomycins include mitomycin D and mitomycin E [disclosed in JP-A-122797/79], mitomycin F and mitomycin J [disclosed in JP-A-45322/80], mitomycin G, mitomycin H and mitomycin K [disclosed in JP-A-118396/80]. The structures of the above-mentioned mitomycins originating from naturally-occurring substances are shown in the following Table 1.

Further, by using these mitomycins as starting materials, various other mitomycins which are not occurring naturally have been synthesized such as, for example, 9a-O-demethylmitomycin G [disclosed in JP-A-15408/80], 1a-demethylmitomycin G and 1a-demethylmitomycin K [disclosed in JP-A-7787/81] and 9-epi-mitomycin B and 9-epi-mitomycin D [disclosed in JP-A-30978/81], the structures of which are shown in Table 2.

TABLE 1
Structures of naturally-occurring mitomycins

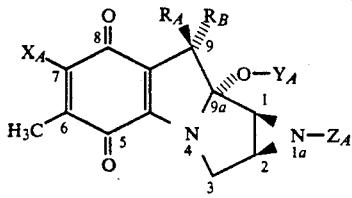

| MM* | $X_A$ | $Y_A$ | $Z_A$ | $R_A$ | $R_B$ |
|---|---|---|---|---|---|
| A | $OCH_3$ | $CH_3$ | H | $CH_2OCONH_2$ | H |
| B | $OCH_3$ | H | $CH_3$ | H | $CH_2OCONH_2$ |
| C | $NH_2$ | $CH_3$ | H | $CH_2OCONH_2$ | H |
| D | $NH_2$ | H | $CH_3$ | H | $CH_2OCONH_2$ |
| E | $NH_2$ | $CH_3$ | $CH_3$ | H | $CH_2OCONH_2$ |
| F | $OCH_3$ | $CH_3$ | $CH_3$ | $CH_2OCONH_2$ | H |
| G | $NH_5$ | $CH_3$ | $CH_3$ | bonded together | $=CH_2$ |
| H | $OCH_3$ | H | $CH_3$ | bonded together | $=CH_2$ |
| J | $OCH_3$ | $CH_3$ | $CH_3$ | H | $CH_2OCONH_2$ |
| K | $OCH_3$ | | $CH_3$ | bonded together | $=CH_2$ |
| P** | $NH_2$ | $CH_3$ | $CH_3$ | $CH_2OCONH_2$ | H |

[*mitomycin: **porfiromycin]

TABLE 2
Structures of synthetic mitomycins

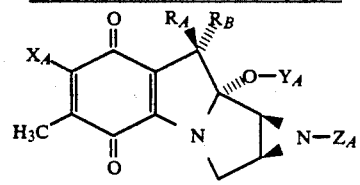

| Mitomycins | $X_A$ | $Y_A$ | $Z_A$ | $R_A$ | $R_B$ |
|---|---|---|---|---|---|
| 9a-O-demethyl1MG | $NH_2$ | H | $CH_3$ | bonded together | $=CH_2$ |
| 1a-demethyl1MG | $NH_2$ | $CH_3$ | H | bonded together | $=CH_2$ |
| 1a-demethyl1MK | $OCH_3$ | $CH_3$ | H | bonded together | $=CH_2$ |

TABLE 2-continued
Structures of synthetic mitomycins

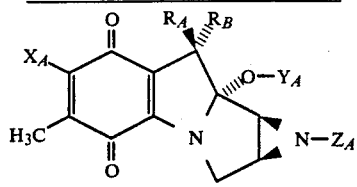

| Mitomycins | $X_A$ | $Y_A$ | $Z_A$ | $R_A$ | $R_B$ |
|---|---|---|---|---|---|
| 9-epiMB | $OCH_3$ | H | $CH_3$ | $CH_2OCONH_2$ | H |
| 9-epiMD | $NH_2$ | H | $CH_3$ | $CH_2OCONH_2$ | H |

Notes:-
MG - mitomycin G; MK - mitomycin K; MB - mitomycin B
MD - mitomycin D

The above-mentioned mitomycins include some having excellent anti-tumour activity, which have, however certain undesirable side effects such as causing a decrease in the number of leucocytes. Thus, attempts have been made to prepare, synthetically, mitomycin derivaties having higher activity or reduced toxicity.

(6-halo)-7-ethylenedioxymitomycins viz. compounds of the following formula (III), which may serve as starting materials for compounds of the present invention, are disclosed in our copending EP-A-0,284,380.

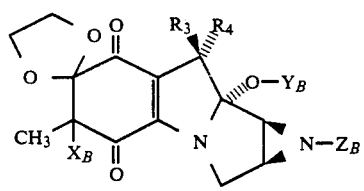

[wherein
$X_B$ represents hydrogen or halogen; $Y_B$ is hydrogen or methyl;
$Z_B$ represents hydrogen, methyl or acyl;
one of $R_3$ and $R_4$ is carbamoyloxymethyl and the other is hydrogen, or $R_3$ and $R_4$ are combined together to form methylene.]

There is a continuing need for further mitomycin derivatives having anti-bacterial and/or anti-tumour activities.

One aspect of the present invention thus provides novel mitomycin derivatives having excellent anti-tumour activity, represented by the formula (I)

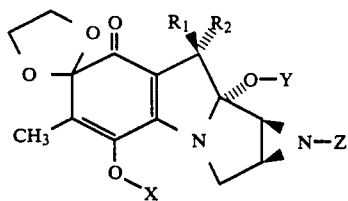

[wherein
X is acyl, lower alkyl, alkoxycarbonyl, aryloxycarbonyl or aralkoxycarbonyl;
Y is hydrogen or methyl;
Z is hydrogen, methyl, acyl or allyloxycarbonyl;
one of $R_1$ and $R_2$ represents carbamoyloxymethyl and the other represents hydrogen, or $R_1$ and $R_2$ together represent methylene.]

The present invention further provides intermediates for the preparation of compounds (I), represented by the formula (II):

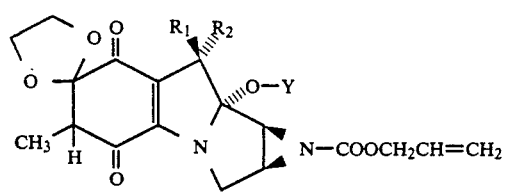

[wherein
Y is hydrogen or methyl;
one of $R_1$ and $R_2$ represents carbamoyloxymethyl and the other represents hydrogen, or $R_1$ and $R_2$ together represent methylene.]

When X or Z is acyl, such group has the structure RCO where R is hydrogen, straight or branched alkyl having 1–17 carbon atoms, alkenyl having 2–17 carbon atoms, aralkyl or unsubstituted or substituted aryl groups, the alkylene chain of said alkyl and alkenyl groups optionally being interrupted by from 1 to 3 oxygen atoms or carbonyl groups.

Aralkyl groups are exemplified by benzyl and phenethyl.

Preferred aryl groups are exemplified by phenyl and naphthyl, and may be substituted by, for example, lower alkyl having 1–3 carbon atoms such as methyl, ethyl and propyl; halogen atoms such as fluorine, chlorine and bromine; and nitro.

Preferred acyl groups are exemplified by formyl, acetyl, trimethylacetyl, propionyl, butyryl, hexanoyl, octanoyl, dodecanoyl, stearoyl, oleoyl, linoleoyl, benzylcarbonyl, benzoyl, p-nitrobenzoyl, naphthoyl, 3,6,9-trioxadecanoyl and 2-acetylpropionyl groups.

In the definition of X, lower alkyl groups are exemplified by straight or branched alkyl having 1–6 carbon atoms such as methyl, ethyl, propyl, butyl, pentyl and hexyl.

When X is alkoxycarbonyl, aryloxycarbonyl or aralkoxycarbonyl, it may have the structure ROCO, where R has the same meaning as defined above other than hydrogen or alkenyl.

Preferred examples of such groups include methoxycarbonyl, ethoxycarbonyl, propoxycarbonyl, butoxycarbonyl, hexyloxycarbonyl, octyloxycarbonyl, dodecyloxycarbonyl, octadecyloxycarbonyl, benzyloxycarbonyl, phenoxycarbonyl and p-nitrophenoxycarbonyl.

Compounds (I) may be prepared by the following processes.

PROCESS-1

Synthesis of Compounds (I-1) viz. Compounds (I) wherein X is acyl:

Synthesis of Compounds (I-1) may be effected by the reaction of Compounds (II) or Compounds (III-1) viz. Compounds (III) wherein $X_B$ is hydrogen, with an acylating agent in the presence of a base.

Compounds which may be used for this reaction are exemplified by certain mitomycins such as 7-demethoxy-6,7-dihydro-7-ethylenedioxymitomycin A, 1a-acetyl-7-demethoxy-6,7-dihydro-7-ethylenedioxymitomycin A, 1a-allyloxycarbonyl-7-demethoxy-6,7-dihydro-7-ethylenedioxymitomycin A, 7-demethoxy-6,7-dihydro-7-ethylenedioxymitomycin B and 7-demethoxy-6,7-dihydro-7-ethylenedioxymitomycin F.

For carrying out the reaction, any solvent may be used which can dissolve the mitomycin used as starting material. Examples of preferred solvents include dimethylformamide, tetrahydrofuran, chloroform, methylene chloride and acetonitrile. They may be used alone or in admixture.

Examples of the preferred bases used for the reaction include various organic bases such as triethylamine and pyridine, which may be used in an amount of more than equimolar (preferably 2–10 molar equivalents) per mole of mitomycin. If desired one may also use an excess of pyridine as both the base and solvent.

Acylating agents which may be used include, for example, various reactive derivatives of the corresponding carboxylic acids such as acid anhydrides and acid halides, preferred examples being acetic anhydride, octanoyl chloride, dodecanoyl chloride, benzoyl chloride, trimethylacetyl chloride, 3,6,9-trioxadecanoyl chloride, 2-acetylpropionyl chloride, linoleoyl chloride and linoleic anhydride.

The reaction may be effected e.g. at a temperature of from $-20°$ to $70°$ C., preferably $0°–30°$ C. and completed in a period of 4 hours to 4 days. Completion of the reaction may readily be monitored by thin layer chromatography (TLC) on silica gel.

The reaction mixture may be used without any further processing. However, if desired, the reaction mixture may be neutralized, for example with phosphate buffer (pH 7.0), followed by extraction with a non-aqueous solvent such as, for example, chloroform, methylene chloride or ethyl acetate. After washing with, for example, water or aqueous sodium chloride, the extract is concentrated and purified. The purification may be effected, for example, by silica gel column chromatography, TLC and high performance liquid chromatography (HPLC) using chemical-coupled porous silica as a carrier.

PROCESS-2

Synthesis of Compounds (I-2) viz. Compounds (I) wherein X is alkyl:

Synthesis of Compounds (I-2) may be effected by the reaction of Compounds (II) or Compounds (III-2) viz. Compounds (III) wherein $X_B$ is hydrogen and $Z_B$ is methyl or acyl, with an alkylating agent in the presence of a base.

The solvents which may be used for the acylation reaction in Process-1 may also be used for this reaction.

Examples of the bases used for the reaction include inorganic bases such as potassium carbonate and sodium carbonate, which may be used in above an equimolar amount, preferably 4–10 moles per mole of mitomycin.

Examples of the alkylating agents which may be used include alkyl halides and dialkyl sulfates such as methyl iodide, dimethyl sulfate and diethyl sulfate.

Usually the reaction is carried out at a temperature of from $0°$ to $30°$ C. for several days. After completion of reaction, the reaction mixture may be worked up in a similar manner as for Process-1.

PROCESS-3

Synthesis of Compounds (I-3) viz. Compounds (I) wherein X is alkoxycarbonyl, aryloxycarbonyl or aralkoxycarbonyl:

Synthesis of Compounds (I-3) may be effected by the reaction of Compounds (II) or (III-2) with an alkoxycarbonylating, aryloxycarbonylating or aralkoxycarbonylating agent in the presence of a base.

The solvents and bases which may be used for Process-1 may also be used for this process.

Preferred carbonylating agents include the corresponding reactive derivatives of carbonic acid esters such as acid anhydrides and acid halides, for instance ethyl chloroformate, dodecyl chloroformate and di-t-butyl dicarbonate. Work-up and purification may be effected in a similar manner to that used in Process-1.

PROCESS-4

Synthesis of Compounds (I-4) viz. Compounds (I) wherein Z is hydrogen:

(a) Synthesis of Compounds (I-4) may be effected by the reaction of Compounds (I) wherein Z is acyl with a deacylating agent used as a base.

Examples of the bases which may be used for this process include amines such as ammonia and inorganic bases such as sodium bicarbonate.

The preferred solvent is water.

The reaction is generally complete in 10-20 hours. The reaction mixture may be worked up and purified, for example, by silica gel column chromatography in conventional manner.

(b) Alternatively, synthesis of Compounds (I-4) may be effected by the reaction of Compounds (I-5) viz. Compounds (I) wherein Z is allyloxycarbonyl, with a reducing agent in the presence of a palladium catalyst.

Any and all palladium catalysts may be used for the reaction provided that they comprise a zerovalent homogeneous system. Examples of preferred catalysts include tetrakis(triphenylphosphine)palladium(0) and palladium(II) acetatetriphenylphosphine. One may use e.g. 0.01-1.0 mole, preferably 0.1-0.5 mole of catalyst based on the Compound (I-5).

Suitable reducing agents are exemplified by formic acid, triethylammonium formate, tributyltin hydride, triphenyltin hydride, trimethylhydrosilane and sodium borohydride.

Examples of solvents which may be used include diethylether, tetrahydrofuran, acetonitrile and dimethylformamide, which may be used alone or in admixture.

The reaction may be effected at a temperature of e.g. from $-20°$ to $80°$ C., preferably $0°$-$30°$ C. for a period of from 10 minutes to 5 hours.

After completion of reaction, the reaction mixture may be worked up in a similar manner to that used in Process-1.

Compounds (II) viz. the intermediates for the synthesis of Compounds (I) may be prepared in the following manner.

PROCESS: SYNTHESIS OF COMPOUNDS (II)

The synthesis of Compounds (II) may be effected by the reaction of Compounds (III-3) viz. Compounds (III) wherein both $X_B$ and $Z_B$ represent hydrogen, with an allyloxycarbonylating agent in the presence of a base.

Examples of suitable allyloxycarbonylating agents include allyl chloroformate and diallyl dicarbonate, which may be used in at least an equimolar amount, preferably 1.0-1.5 moles per mole of Compound (III-3).

The reaction may be effected at a temperature of from $-78°$ to $70°$ C., preferably from $-20°$ to $30°$ C. for a period of from 5 minutes to 5 hours.

Similar solvents, bases and work-up used for Process-1 may be used for this process.

It will be understood that the above-mentioned processes do not limit the scope of the present invention.

Compounds of the present invention are cytotoxic agents and may be used as anti-tumour agents. They also exhibit anti-bacterial activity.

Compounds (I) may be used in various forms suitable for pharmacological administration, with or without further formulation. Generally, pharmaceutical compositions will comprise an effective amount of a Compound (I) and a pharmacologically acceptable carrier and/or adjuvant. For example, Compounds (I) may be formulated into an injectable composition by dissolving in a pharmaceutically acceptable diluent such as, for example, physiological saline or in an injection solution of glucose, lactose or mannitol.

The composition may also take the form of freeze-dried injectable compositions or injection powders containing sodium chloride, e.g. as standardised by the Pharmacopoeia of Japan; such compositions are dissolved in a suitable liquid carrier prior to use. The injectable compositions may comprise, if desired, various additives such as, for example, polyethylene glycol, HCO-60 (surfactant: commercial product of Nikko Chemicals K.K., Japan), ethanol and/or carriers such as, for example, liposome, cyclodextrin and the like. Usually, the injectable compositions are used for intravenous injection, although it is possible to administer them into an artery, the abdominal cavity or the thorax.

It is possible to prepare tablets, granules, powders and elixirs for oral administration by mixing Compounds (I) with suitable excipients, disintegrators, binders and lubricants, followed by formulating in conventional manner. If desired, it is also possible to use Compounds (I) as suppositories by mixing with pharmaceutically acceptable carriers and formulating the mixture in a conventional manner.

The dose of Compound (I) may vary, depending upon the administration schedule, type of Compound (I) used, and the age and symptoms of the patient; the dosage regimen may also be varied depending upon the symptoms and the dosage administered.

Thus, it is possible to administer the compound intermittently, for example, once per week or once per three weeks at a dose of 0.06-6 mg/kg.

The following Examples and Preparations illustrate the invention, in which the physicochemical characteristics of each compound were determined by means of the following instruments:

'H-NMR: Bruker AM-400 (400 MHz), measured in deuterochloroform, unless otherwise specified; and JEOL JMN-GX270 (270 MHz), measured in deuteropyridine.

MS: Hitachi M-80B Mass Spectrometer (commercial product of Hitachi Ltd., Japan), measured by the SI method; and JEOL JMS-D300, measured by the FAB method.

IR: IR-810 Infrared Spectrometer (commercial product of Nihon Bunko K.K., Japan), measured by the KBr method.

TLC: Thin layer chromatography using Art 5744 (commercial product of Merck AG., West Germany) and developed by a solvent system of chloroform/methanol (9:1 v/v), unless otherwise specified.

Table 3 indicates the structures of typical Compounds (I) obtained by synthesis:

TABLE 3

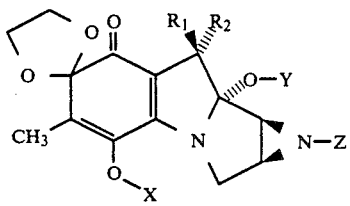

| Comp. No. (Ex. No.) | $R_1$ | $R_2$ | X | Y | Z |
|---|---|---|---|---|---|
| 1 (1) | $CH_2OCONH_2$ | H | $CH_3CO$ | $CH_3$ | $COCH_3$ |
| 2 (2) | $CH_2OCONH_2$ | H | $CH_3CO$ | $CH_3$ | H |
| 3 (3) | H | $CH_2OCONH_2$ | $CH_3CO$ | H | $CH_3$ |
| 4 (4) | $CH_2OCONH_2$ | H | C₆H₅-CO | $CH_3$ | $COCH_3$ |
| 5 (5) | $CH_2OCONH_2$ | H | C₆H₅-CO | $CH_3$ | H |
| 6 (6) | $CH_2OCONH_2$ | H | $CH_3(CH_2)_{10}CO$ | $CH_3$ | H |
| 7 (7) | $CH_2OCONH_2$ | H | $CH_3$ | $CH_3$ | H |
| 9 (9) | $CH_2OCONH_2$ | H | CH₃(CH=CHCH₂)₄CH₂CO | $CH_3$ | $CO_2CH_2CH=CH_2$ |
| 10 (10) | $CH_2OCONH_2$ | H | CH₃(CH=CHCH₂)₄CH₂CO | $CH_3$ | H |
| 11 (11) | $CH_2OCONH_2$ | H | $CH_3(CH_2)_6CO$ | $CH_3$ | H |
| 12 (12) | $CH_2OCONH_2$ | H | $(CH_3)_3CCO$ | $CH_3$ | H |
| 13 (13) | $CH_2OCONH_2$ | H | $CH_3OCH_2CH_2OCH_2CH_2OCH_2CO$ | $CH_3$ | H |
| 14 (14) | $CH_2OCONH_2$ | H | $CH_3COCH_2CH_2CO$ | $CH_3$ | H |
| 15 (15) | $CH_2OCONH_2$ | H | $CH_3CH_2OCO$ | $CH_3$ | H |

EXAMPLE 1

Compound "a" (400 mg; obtained in Preparation 1) was dissolved in chloroform (5.0 ml), and triethylamine (0.5 ml) and acetic anhydride (0.2 ml) were added thereto. The mixture was stirred at a temperature of 20° C. for 30 hours. After addition of methanol (2.0 ml), the solvent was removed by evaporation under reduced pressure. The residue was subjected to silica gel column chromatography using a solvent system of chloroform/methanol (95:5 v/v). The eluted yellow fractions were collected, from which the solvent was removed by evaporation under reduced pressure to obtain Compound 1 (170 mg) with a yield of 39%.

$^1$H-NMR: 400 MHz, δ (ppm).

Main peaks 3.14 (s, 3H), 2.27 (s, 3H), 2.12 (s, 3H), 1.72 (s, 3H).

EXAMPLE 2

Compound 1 (170 mg; obtained in Example 1) was dissolved in tetrahydrofuran (50 ml), to which was added an aqueous solution of sodium bicarbonate (10 ml). The mixture was stirred at room temperature for 15 hours. Chloroform (100 ml) was added to the reaction solution. The water layer was extracted with chloroform to give a chloroform layer. The chloroform layer was washed with a saturated solution of sodium chloride, and then dried by using anhydrous sodium sulfate. The residue was subjected to silica gel column chromatography by using a solvent system of chloroform/methanol (95:5 v/v). The eluted yellow fractions were collected, from which the solvent was removed by evaporation under reduced pressure to obtain Compound 2 (92 mg) with a yield of 59%.

TLC: Rf=0.31.

SI-MS: m/z 422(M+1) $C_{19}H_{23}N_3O_8$=421.

IR: cm$^{-1}$ 3450, 1770, 1720, 1671, 1612, 1550, 1490, 1460, 1340, 1190, 1074, 970, 854, 805.

$^1$H-NMR: 400 MHz, δ (ppm) 4.65 (dd, J=10.8, 4.2 Hz, 1H), 4.64 (brs, 2H), 4.56–4.44 (m, 3H), 4.19–4.13(m, 2H), 3.80 (d, J=11.3 Hz, 1H), 3.51 (dd, J=10.8, 4.4 Hz, 1H), 3.33 (brd, J=11.6 Hz, 1H), 3.16 (s, 3H), 2.88(d, J=4.2 Hz, 1H), 2.78 (brs, 1H), 2.29 (s, 3H), 1.72 (s, 3H), ~0.7 (br, 1H).

EXAMPLE 3

Compound "b" (270 mg; obtained in Preparation 2), pyridine(10 ml) and acetic anhydride (0.5 ml) were treated in a similar manner to that described in Example 1 to obtain Compound 3 (120 mg) with a yield of 40%.

TLC: Rf=0.40.

SI-MS: m/z 424(M+3) $C_{19}H_{23}N_3O_8=421$.

IR: $cm^{-1}$ 3560, 3420, 3184, 2884, 1753, 1706, 1630, 1601, 1533, 1506, 1499, 1459, 1345, 1221, 1210, 1173, 1131, 1067, 1013, 964, 821, 738.

$^1$H-NMR: 400 MHz, (pyridine-$d_5$) δ (ppm) 7.26 (br, 2H), 5.54 (dd, J=10.6, 3.7 Hz, 1H), 5.08 (t, J=10.8 Hz, 1H), 4.68–4.52 (m, 2H), 4.15 (dd, J=10.6, 4.7 Hz, 1H), 4.14–4.07 (m, 2H), 3.78 (d, J=11.6 Hz, 1H), 3.46 (dd, J=11.6, 2.2Hz. 1H). 2.43 (d, J=4.7 Hz, 1H), 2.22 (dd, J=4.7, 2.2 Hz, 1H), 2.19 (s, 3H), 2.07 (s, 3H), 1.78 (d, J=0.5 Hz, 3H).

EXAMPLE 4

Compound "a" (186 mg; obtained in Preparation 1), chloroform (10 ml), triemthylamine (0.3 ml), dimethylaminopyridine (1 mg) and benzoyl chloride (0.1 ml) were treated in a similar manner to that described in Example 1 to obtain Compound 4 (136 mg) with a yield of 59%.

$^1$H-NMR: 400 MHz, δ (ppm). Main peaks, 8.30–7.50. (m, 5H), 3.20 (s, 3H), 2.16 (s, 3H) 1.83 (s, 3H).

EXAMPLE 5

Compound 4 (136 mg; obtained in Example 4) was combined with methanol (20 ml) and ammonia (0.5 ml in 6.8M of methanol solution) and stirred for 4 hours. The solvent was removed by evaporation under reduced pressure, and then the residue was subjected to silica gel chromatography using a solvent system of chloroform/methanol (98:2–95:5 v/v). The eluted yellow fractions were collected and combined. After removal of the solvent by evaporation under reduced pressure, there was obtained Compound 5 (42 mg) with a yield of 33%.

TLC: Rf=0.44.

SI-MS: m/z 484(M+1) $C_{24}H_{25}N_3 O_8=483$.

IR: $cm^{-1}$ 3450, 3350, 2902, 1738, 1716, 1610, 1547, 1482, 1452, 1388, 1321, 1260, 1177, 1070, 1054, 1022, 972, 856, 801, 709.

$^1$H-NMR: 400 MHz, δ (ppm) 8.16 (m, 2H), 7.69 (m, 1H), 7.55 (m, 2H), 4.70 (br, 2H), 4.66 (dd, J=10.6, 4.2 Hz, 1H), 4.59–4.47 (m, 3H), 4.21–4.16 (m, 2H), 3.78 (d, J=11.6 Hz, 1H), 3.54 (dd, J=10.6, 4.2 Hz, 1H), 3.19 (s, 3H), 3.13 (brd, J=11.3 Hz, 1H), 2.86 (brd, J=4.2 Hz, 1H), 2.69 (br. 1H), 1.78 (s, 3H), 0.68 (br, 1H).

EXAMPLE 6

Compound "a" (321 mg; obtained in Preparation 1), chloroform (14 ml), triethylamine (0.5 ml). dimethylaminopyridine (5 mg) and dodecanoyl chloride (0.176 ml) were treated in a similar manner to that described in Example 1 to obtain Compound 6 (280 mg; 1a-acetylated) with a yield of 61%.

In a similar manner to that described in Example 5. Compound 6 (67 mg) was obtained with a yield of 28% by using methanol (40 ml) and ammonia (0.6 ml in 6.8M of methanol solution).

TLC: Rf=0.47.

SI-MS: m/z 562(M+1) $C_{29}H_{43}N_3O_8=561$.

IR: $cm^{-1}$ 3458, 3350, 3306, 2926, 2854, 1767, 1717, 1610, 1545, 1483, 1454, 1391, 1326, 1181, 1133, 1074, 1013, 972, 936, 893, 857, 801, 712.

$^1$H-NMR: 400 MHz, δ (ppm) 4.77 (br, 2H), 4.64 (dd, J=10.6, 4.2 Hz, 1H), 4.56–4.44 (m, 3H), 4.19–4.13 (m, 2H), 3.78 (d, J=11.3 Hz, 1H), 3.50 (dd, J=10.6, 4.2 Hz, 1H), 3.30 (brd, J=11.3 Hz, 1H), 3.15 (s, 3H), 2.88 (br, 1H), 2.78 (br, 1H), 2.53 (m, 2H), 1.72 (m, 2H), 1.71 (s, 3H), 1.68–1.40 (m, 16H), 0.88 (t, J=6.6 Hz, 3H), 0.73 (br, 1H).

EXAMPLE 7

Compound "a" (197 mg; obtained in Preparation 1) was dissolved in methylene chloride (8 ml). Then, potassium carbonate (300 mg) and dimethyl sulfate (0.2 ml) were added thereto. The mixture was stirred at room temperature for 2 days and was added to an aqueous solution of sodium bicarbonate, followed by extraction with chloroform. After washing with a saturated solution of sodium chloride, the chloroform layer was dried by using anhydrous sodium sulfate.

The solvent was removed by evaporation under reduced pressure. The residue was subjected to silica gel column chromatography using a solvent system of chloroform/metanol (97:3 v/v) to obtain Compound 7 (68 mg; 1 a-acetylated) with a yield of 33%. 97 mg of the starting material was recovered.

The resultant 1a-acetylated Compound 7 (64 mg). methanol (30 ml) and ammonia (1.5 ml of 6.8M of methanol solution) were treated in a similar manner to that described in Example 5. The acetyl group was removed from the product to obtain Compound 7 (55 mg) with a yield of 93%.

TLC: Rf=0.38.

SI-MS: m/z 394(M+1) $C_{18}H_{23}N_3O_7=393$.

IR: $cm^{-1}$ 3430, 3300, 2940, 2998, 1709, 1659, 1611, 1541, 1474, 1452, 1387, 1332, 1288, 1178, 1137, 1066, 1033, 964, 856, 823, 801, 763, 709, 660.

$^1$H-NMR: 400 MHz, δ (ppm) 4.77 (br, 2H), 4.68 (dd, J=10.6, 4.2 Hz, 1H), 4.54–4.43 (m, 3H), 4.18–4.13 (m, 2H), 4.09 (d, J=12.3 Hz, 1H), 3.65 (s, 3H), 3.51 (dd, J=8.9, 4.4 Hz, 1H), 3.47 (brd, J=12.5 Hz, 1H), 3.21 (s, 3H), 2.89 (br, 1H), 2.79 (br, 1H), 1.83 (s, 3H), 0.70 (br, 1H).

EXAMPLE 8

1a-allyloxycarbonyl-7-demethoxy-6,7-dihydro-7-ethylenedioxymitomycin A (Compound 8):

7-demethoxy-6,7-dihydro-7-ethylenedioxymitomycin A (3.81 g) was dissolved in a mixture of anhydrous chloroform (100 ml) and anhydrous pyridine (1.0 ml). A solution of anhydrous chloroform (10 ml) containing allyloxycarbonyl chloride (1.1 ml) was added dropwise thereto in 15 minutes while stirring at a temperature of 0° C. After this, the solution was stirred at a temperature of 0° C. for 30 minutes, followed by further stirring at a temperature of 25° C. for 15 minutes.

After diluting with chloroform, the reaction solution was in turns washed with a saturated aqueous solution of sodium bicarbonate, a saturated aqueous solution of ammonium chloride and a saturated aqueous solution of sodium chloride, and was then dried by using anhydrous sodium sulfate. After removal of the drying agent by filtration, the solvent was removed from the material by evaporation under reduced pressure. The residue was subjected to silica gel column chromatography using a solvent system of chloroform/methanol (30:1 v/v) to elute yellowish pink fractions.

After removal of the solvent by evaporation under reduced pressure, the residue was dissolved in a small amount of chloroform. After addition of n-hexane to the solution to precipitate a powder, the solvent was removed from the powder by evaporation under reduced pressure, followed by drying well in vacuo. There was obtained Compound 8 (3.66 g) in the form of yellowish pink powder with a yield of 79%.

It was found that Compound 8 was a mixture of two compounds having different stereochemical structures at $C_6$-position (diastereoisomers), of which ratio was about 2.5:1 calculated on the basis of NMR data (hereinafter the ratio of two substances was measured with reference to NMR data).

TLC: (Art 5715) Rf=0.45 (chloroform/methanol=15:1 v/v).

FAB-MS: m/z 464(M+ +1) $C_{21}H_{25}N_3O_9$=463.

IR: $cm^{-1}$ 3460, 2950, 2900, 1730, 1650, 1580, 1450, 1400, 1330, 1270, 1190, 1090, 1070, 1030.

$^1$H-NMR: 270 MHz, δ (ppm). Major; 7.5–7.3 (bs, 2H), 6.10–5.87 (m, 1H), 5.68 (dd, J=10.7, 4.7 Hz, 1H), 5.34 (dd, J=17.3, 1.6 Hz, 1H), 5.15 (dd, J=10.5, 1.2 Hz, 1H), 4.80 (t, J=11.0 Hz, 1H), 4.68 (d, J=5.9 Hz, 2H), 4.54–3.87 (m, 6H), 3.84 (d, J=4.4 Hz, 1H), 3.56–3.41 (m, 2H), 3.39 (q, J=6.8 Hz, 1H), 3.11 (s, 3H), 1.31 (d, J=7.0 Hz, 3H). Minor: main peaks 7.5–7.3 (bs, 2H), 6.10–5.87 (m, 1H), 5.68 (dd, J=10.7, 4.7 Hz, 1H), 5.29 (dd, J=17.2, 1.6 Hz, 1H). 5.09 (dd, J=9.5, 1.1 Hz, 1H), 4.80 (t, J=11.0 Hz, 1H), 4.59 (d, J=5.7 Hz, 2H), 3.84 (d, J=4.4 Hz, 1H), 3.15 (s, 3H), 1.29 (d, J=7.0 Hz, 3H).

EXAMPLE 9

Compound 8 (236 mg; obtained in Example 8) was dissolved in a mixture of anhydrous acetonitrile (10 ml) and anhydrous triethylamine (1.8 ml). Linoleoyl chloride (0.47 ml) and dimethylaminopyridine (5 mg) were added thereto, followed by stirring at room temperature for 18 hours.

After dissolving in a phosphate-buffered solution (0.05M; pH 7.0), the reaction solution was extracted three times with chloroform. The chloroform layer was washed in turns, using a saturated aqueous solution of sodium bicarbonate, a saturated aqueous solution of ammonium chloride and a saturated aqueous solution of sodium chloride, and was then dried by using anhydrous sodium sulfate. After removal of the drying agent by filtration, the solvent was removed from the material by evaporation under reduced pressure. The residue was subjected to silica gel column chromatography using a solvent system of chloroform/methanol (from 100:1 to 50:1 v/v) to elute yellow fractions. After removal of the solvent by evaporation under reduced pressure, the residue was dissolved in a small amount of chloroform. n-Hexane was added thereto to precipitate a powder from which the solvent was then removed by evaporation under reduced pressure. The material was well dried in vacuo to obtain Compound 9 (291 mg) in the form of yellow powder with a yield of 79%.

TLC: (Art 5715) Rf=0.38 (chloroform/methanol=20:1 v/v).

IR: $cm^{-1}$ 3450, 3350, 3300, 2930, 2860, 1770, 1720, 1610, 1540, 1490, 1460, 1400, 1330, 1180, 1120, 1080.

$^1$H-NMR: 270 MHz, δ (ppm) 7.7–7.3 (br, 2H), 6.12–5.97 (m, 1H), 5.63 (dd, J=10.4, 4.4 Hz, 1H), 5.58–5.44 (m, 4H), 5.32 (dd, J=17.2, 1.5 Hz, 1H), 5.2–5.0 (m, 1H), 4.72 (t, J=11.0 Hz, 1H), 4.67 (d, J=5.9 Hz, 2H), 4.72–4.59 (m, 2H), 4.25–4.14 (m, 2H), 4.09 (d, J=12.1 Hz, 1H), 3.90 (dd, J=11.4, 4.4 Hz, 1H), 3.85 (d, J=4.8 Hz, 1H), 3.60 (dd, J=4.6, 1.6 Hz, 1H), 3.53 (dd, J=12.1, 1.8 Hz, 1H), 3.10 (s, 3H), 2.93 (m, 2H), 2.77–2.59 (m, 2H), 2.16–2.05 (m, 4H), 1.90 (s, 3H), 1.83–1.63 (m, 2H), 1.45–1.15 (m, 14H), 0.87 (bt, 3H).

EXAMPLE 10

Compound 9 (270 mg; obtained in Example 9) was dissolved in anhydrous tetrahydrofuran (10 ml). Triethyl ammonium formate (150 μl) and tetrakis(triphenylphosphine)palladium(0) (40 mg) were added thereto in an argon atmosphere, and the mixture was stirred at a temperature of 25° C. for 50 minutes.

After diluting with chloroform, the diluted solution was washed in turns using a saturated aqueous solution of sodium bicarbonate, a saturated aqueous solution of ammonium chloride and a saturated aqueous solution of sodium chloride, and was then dried by using anhydrous sodium sulfate. After removal of the drying agent by filtration, the solvent was removed from the material by evaporation under reduced pressure. The residue was purified by silica gel column chromatography using a solvent system of chloroform/methanol (50:1 v/v) to elute yellow fractions.

The solvent was removed from the resultant material by evaporation. Then, diethylether was added to the material to remove the solvent further. The resultant powder was well dried in vacuo to obtain Compound 10 (183 mg) in the form of yellow powder with a yield of 76%.

TLC: (Art 5715) Rf=0.25 (chloroform/methanol=20:1 v/v).

FAB-MS: m/z 642 (M+ +1) $C_{35}H_{51}N_3O_8$=641.

IR: $cm^{-1}$ 3450, 3350, 3300, 2920, 2850, 1760, 1710, 1610, 1540, 1480, 1450, 1390, 1330, 1070.

$^1$H-NMR: 270 MHz. δ (ppm) 7.7–7.4 (br, 2H), 5.57–5.40 (m, 4H), 5.43 (dd, J=10.3, 4.2 Hz, 1H), 5.10 (t, J=10.6 Hz, 1H), 4.71–4.61 (m, 2H), 4.20–4.14 (m, 2H), 3.94 (d, J=10.4 Hz, 1H), 3.89 (dd, J=11.1, 4.0 Hz, 1H), 3.48 (bd, J=11.5 Hz, 1H), 3.2–3.1 (m, 1H), 3.14 (s, 3H), 2.93 (m, 2H), 2.80 (bs, 1H), 2.66 (dt, J=7.3, 3.7 Hz, 2H), 2.23–2.07 (m, 5H), 1.88 (s, 3H), 1.83–1.68 (m, 2H), 1.45–1.20 (m, 14H), 0.86 (t, J=6.7 Hz, 3H).

EXAMPLE 11

Compound 8 (117 mg; obtained in Example 8) was dissolved in a mixture of anhydrous acetonitrile (5.0 ml) and anhydrous triethylamine (0.60 ml). Then octanoyl chloride (122 mg) and dimethylaminopyridine (5 mg) were added thereto. The mixture was stirred for 8 hours at room temperature.

The reaction solution was diluted with chloroform and washed in turns using saturated aqueous solutions of sodium bicarbonate (twice), saturated aqueous solutions of ammonium chloride (twice) and a saturated aqueous solution of sodium chloride (once), followed by drying with anhydrous sodium sulfate. After removal of the drying agent by filtration, the solvent was removed from the material by evaporation under reduced pressure. The residue was well dried in vacuo (Step-1).

The resultant residue was dissolved in anhydrous tetrahydrofuran (5.0 ml), and triethyl ammonium formate (50 μl) and tetrakis(triphenylphosphine)palladium(0) (30 mg) were added thereto in an argon atmosphere. The mixture was stirred at a temperature of 25° C. for one hour.

After removal of the solvent from the reaction solution by evaporation under reduced pressure, the residue was purified by silica gel column chromatography using a solvent system of chloroform/methanol (30:1 v/v) to give yellow fractions, from which the solvent was then removed by evaporation under reduced pressure. The material was well dried in vacuo to obtain Compound 11 (87.8 mg) in the form of yellow crystals with a yield of 69% (Step-2).

TLC: (Art 5715) Rf=0.33 (chloroform/methanol=15:1 v/v).

FAB-MS: m/z 506 $C_{25}H_{35}N_3O_8=505$.

IR: $cm^{-1}$ 3450, 3340, 3300, 2920, 2860, 1760, 1710, 1600, 1540, 1480, 1450, 1390, 1330, 1070.

$^1$H-NMR: 270 MHz, δ (ppm) 7.8–7.4 (br, 2H), 5.43 (dd, J=10.4, 4.1 Hz, 1H), 5.3–5.0 (m, 1H), 4.73–4.63 (m, 2H), 4.24–4.15 (m, 2H), 3.95 (d, J=11.5 Hz, 1H), 3.89 (dd, J=11.2, 4.2 Hz, 1H), 3.50 (dd, J=11.3, 1.7 Hz, 1H), 3.16 (d, J=4.4 Hz, 1H), 3.14 (s, 3H), 2.82 (dd, J=4.1, 1.6 Hz, 1H), 2.65 (dt, J=7.2, 3.4 Hz, 2H), 2.4–2.0 (br, 1H), 1.88 (s, 3H), 1.78–1.64 (m, 2H), 1.40–1.12 (m, 8H), 0.85 (s, 3H).

EXAMPLE 12

Compound 8 (118 mg; obtained in Example 8), anhydrous acetonitrile (5.0 ml), anhydrous triethylamine (0.60 ml), trimethylacetyl chloride (59.6 mg) and dimethylaminopyridine (1 mg) were treated in a similar manner to that described in Step-1 of Example 11 to produce a crude Compound 12 (1a-allyloxycarbonylated). The whole of the resultant crude product was treated in a similar manner to that described in Step-2 of Example 11 by the use of anhydrous tetrahydrofuran (5.0 ml), triethyl ammonium formate (100 μl) and tetrakis(triphenylphosphine)palladium(0) (70 mg) to obtain Compound 12 (88.7 mg) in the form of yellow crystals with a yield of 75% on the basis of Compound 8.

TLC: (Art 5715) Rf=0.13 (chloroform/methanol=15:1 v/v).

FAB-MS: m/z 464 (M+ +1) $C_{22}H_{29}N_3O_8=463$.

IR: $cm^{-1}$ 3480, 3350, 3270, 2970, 1740, 1710, 1620, 1540, 1480, 1450, 1390, 1340, 1190, 1110, 1070, 970.

$^1$H-NMR: 270 MHz, δ (ppm) 7.8–7.4 (br, 2H), 5.44 (dd, J=10.4, 4.2 Hz, 1H), 5.2–5.1 (m, 1H), 4.72–4.62 (m, 2H), 4.23–4.14 (m, 2H), 3.89 (d, J=11.0 Hz, 1H), 3.87 (dd, J=11.3, 4.3 Hz, 1H), 3.44 (dd, J=10.5 Hz, 1H), 3.17 (bs, 1H), 3.13 (s, 3H), 2.83 (bs, 1H), 2.23 (br, 1H), 1.81 (s, 3H), 1.28 (s, 9H).

EXAMPLE 13

Compound 8 (94.9 mg; obtained in Example 8), anhydrous acetonitrile (2.0 ml), anhydrous triethylamine (0.8 ml), 3,6,9-trioxadecanoyl chloride (210 mg, dissolved in 1.0 ml of anhydrous dichloromethane) and dimethylaminopyridine (5 mg) were treated in a similar manner to that described in Step-1 of Example 11 to produce a crude Compound 13 (1a-allyloxycarbonylated). The whole of the crude product was then treated in a similar manner to that described in Step-2 of Example 11 by using anhydrous tetrahydrofuran (5.0 ml), triethyl ammonium formate (0.10 ml) and tetrakis(triphenylphosphine)palladium(0) (30 mg) to obtain Compound 13. The resultant compound was dissolved in a small amount of chloroform. n-Hexane was added thereto to precipitate a powder for removal of the solvent. The material was dried in vacuo to obtain Compound 12 (22 mg) in the form of yellow powder with a yield of 20% on the basis of Compound 8.

TLC: (Art 5715) Rf=0.13 (ethyl acetate/acetone=1:1 v/v).

FAB-MS: m/z 540 (M+ +1) $C_{24}H_{33}N_3O_{11}=539$.

IR: $cm^{-1}$ 3440, 2900, 1780, 1720, 1620, 1480, 1460, 1390, 1340, 1190, 1110, 1070.

$^1$H-NMR: 270 MHz, (pyridine-d$_5$) δ (ppm) 7.8–7.1 (br, 2H), 5.42 (dd, J=10.4, 4.1 Hz, 1H), 5.08 (bt, 1H), 4.71 (m, 2H), 4.7–4.6 (m, 2H), 4.2–4.1 (m, 2H), 3.92–3.84 (m, 4H), 3.75–3.70 (m, 2H), 3.67–3.63 (m, 2H), 3.54–3.50 (m, 2H), 3.47 (bd, J=10Hz, 1H), 3.28 (s, 3H), 3.13 (bs, 1H), 3.10 (s, 3H), 2.76 (bs, 1H), 2.17 (bs, 1H), 1.84 (s, 3H).

EXAMPLE 14

Compound 8 (95.0 mg; obtained in Example 8), anhydrous acetonitrile (3.5 ml), anhydrous triethylamine (0.80 ml), 2-acetylpropanoyl chloride (76 mg, dissolved in 0.50 ml of anhydrous dichloromethane) and dimethylaminopyridine (3 mg) were treated in a similar manner to that described in Step-1 of Example 11 to produce a crude Compound 14 (1a-allyloxycarbonylated).

The whole of the crude product was treated in a similar manner to that described in Step-2 of Example 11 by the use of anhydrous tetrahydrofuran (5.0 ml), triethyl ammonium formate (0.10 ml) and tetrakis(triphenylphosphine)palladium(0) (19 mg) to produce Compound 14. The compound was obtained as a powder using the procedure described in Example 13. Subsequent drying gave Compound 14 (35.1 mg) in the form of yellow powder with a yield of 36% on the basis of Compound 8.

TLC: (Art 5715) Rf=0.18 (ethyl acetate/acetone=1:1 v/v).

FAB-MS: m/z 478 (M+ +1) $C_{22}H_{27}N_3O_9=477$.

IR: $cm^{-1}$ 3450, 2930, 1770, 1720, 1620, 1530, 1490, 1460, 1410, 1340, 1130, 1080.

$^1$H-NMR: 270 MHz, δ (ppm) 7.7–7.3 (br, 2H), 5.43 (dd, J=10.5, 4.1 Hz, 1H), 5.10 (bt, J=10 Hz, 1H), 4.7–4.6 (m, 2H), 4.2–4.1 (m, 2H), 3.93 (d, J=13.4 Hz, 1H), 3.87 (dd, J=10.9, 4.1 Hz, 1H), 3.70 (bd, J=11.4 Hz, 1H), 3.13 (bs, 1H), 3.13 (s, 3H), 3.0–2.8 (m, 4H), 2.77 (m, 1H), 2.13 (br, 1H), 2.07 (s, 3H), 1.90 (s, 3H).

EXAMPLE 15

Compound 8 (91.5 mg; obtained in Example 8), anhydrous acetonitrile (2.0 ml), anhydrous triethylamine (0.80 ml) and ethyl chloroformate (60 μl) were treated in a similar manner to that described in Step-1 of Example 11 to produce a crude Compound 15 (1a-allyloxycarbonylated).

The whole of the crude compound, anhydrous tetrahydrofuran (5.0 ml), triethyl ammonium formate (0.10 ml) and tetrakis(triphenylphosphine)palladium(0) (20 mg) were treated in a similar manner to that described in Step-2 of Example 11 to give Compound 15. A precipitated powder of the compound was formed and dried in a similar manner to that described in Example 13 to give Compound 15 (66.1 mg) in the form of yellow powder with a yield of 74% on the basis of Compound 8.

TLC: (Art 5715) Rf=0.20.

FAB-MS: m/z 452 (M+ +1) $C_{20}H_{25}N_3O_9=451$.

IR: $cm^{-1}$ 3450, 2970, 2900, 1770, 1720, 1620, 1500, 1480, 1460, 1340, 1240, 1070.

$^1$H-NMR: 270 MHz, δ (ppm) 7.8–7.3 (br, 2H), 5.43 (dd, J=10.3, 4.2 Hz, 1H), 5.09 (bt, J=10 Hz, 1H), 4.7–4.6 (m, 2H), 4.4–4.2 (m, 2H), 4.2–4.1 (m, 2H), 3.96 (d, J=11.9 Hz, 1H), 3.90 (dd, J=11.4, 4.4 Hz, 1H), 3.46 (d, J=11.2 Hz, 1H), 3.15 (bs, 1H), 3.15 (s, 3H), 2.76 (bs, 1H), 2.19 (br, 1H), 1.90 (s, 3H), 1.22 (t, J=7.1 Hz, 3H).

Preparation 1

1a-acetyl-7-demethoxy-6,7-dihydro-7-ethylenedioxymitomycin A (Compound "a"):

1a-acetylmitomycin A (148 mg) was dissolved in a mixture of tetrahydrofuran (3.5 ml) and ethyleneglycol (2 ml). Ethylene glycol (0.5 ml) containing potassium hydroxide (1.6% w/w) was added thereto. The mixture was stirred at a temperature of 25° C. for 5 hours. After addition of an exccess of small pieces of dry-ice while stirring, the reaction solution was diluted with chloroform. The solution was washed with a saturated solution of sodium chloride and dried using anhydrous sodium sulfate. After removal of the solvent by evaporation under reduced pressure, the residue was subjected to silica gel column chromatography using a solvent system of chloroform/methanol (97:3 v/v) to elute yellow fractions. The fractions were collected and the solvent was removed therefrom by evaporation under reduced pressure. The residue was dissolved in a small amount of chloroform. Then, n-hexane was added to the chloroform solution to precipitate a powder from which the solvent was removed by evaporation under reduced pressure. By well drying at a temperature of 25° C. in vacuo, there was obtained Compound "a" (120 mg) in the form of yellow powder with a yield of 75%.

It was found that Compound "a" was a mixture of two compounds having different stereochemical structures at $C_6$-position (diastereoisomers), of which ratio was about 2.5:1.

TLC: (Art 5715) Rf=0.52.

SI-MS: m/z 422 (M+ +1) $C_{19}H_{23}N_3O_8$=421.

IR: $cm^{-1}$ 3480, 3292, 2900, 1720, 1700, 1645, 1575, 1448, 1328, 1268, 1189, 1067, 1031, 949, 859, 749.

$^1$H-NMR: 400 MHz, δ (ppm). Major: 4.98 (dd, J=11.1, 4.9 Hz, 1H), 4.82 (bs, 2H), 4.17 (t, J=11.1 Hz, 1H), 4.41-3.98 (m, 4H), 4.04 (d, J=13.1 Hz, 1H), 3.73 (dd, J=10.8, 4.9 Hz, 1H), 3.50 (d, J=4.4 Hz, 1H), 3.47 (dd, J=13.1, 2.0 Hz, 1H), 3.23 (dd, J=4.4, 2.0 Hz, 1H), 3.22 (q, J=6.6 Hz, 1H), 3.21 (s, 3H), 2.11 (s, 3H), 1.20 (d, J=6.6 Hz, 3H). Minor: main peaks 4.89 (dd, J=10.8, 4.9 Hz, 1H), 4.34 (d, J=13.0 Hz, 1H), 3.42 (dd, J=13.0, 1.7 Hz, 1H), 3.22 (s, 3H), 3.04 (q, J=6.9 Hz, 1H), 2.11 (s, 3H), 1.24 (d, J=6.9 Hz, 3H).

Preparation 2

7-demethoxy-6,7-dihydro-7-ethylenedioxymitomycin B (Compound "b"):

Mitomycin B (230 mg), ethyleneglycol (7.2 ml) and a solution of ethylene glycol (0.5 ml) containing potassium hydroxide (1.6% w/w) were treated in a similar manner to that described in Preparation 1 to obtain Compound "b" (125 mg) in the form of yellow powder with a yield of 50%. It was found that Compound "b" was a mixture of two compounds having different stereochemical structures at $C_6$-position (diastereoisomers), of which ratio was about 4:1.

TLC: (Art 5719) Rf=0.41 and 0.47.

SI-MS: m/z 380 (M+ +1) $C_{17}H_{21}N_3O_7$=379.

IR: $cm^{-1}$ 3450, 2960, 2900, 1718, 1702, 1640, 1570, 1445, 1340, 1204, 1063, 951, 847, 705.

$^1$H-NMR: 400 MHz, δ (ppm). Major: ~4.7 (bs, 2H), 4.73 (dd, J=11.6, 5.7 Hz, 1H), 4.67 (dd, J=11.6, 2.0 Hz, 1H), 4.47 (s, 1H), 4.40 (m, 1H), 4.15-3.95 (m, 3H), 3.75 (dd, J=5.7, 2.0 Hz, 1H), 3.72 (d, J=12.8 Hz, 1H), 3.38 (dd, J=12.8, 2.0 Hz, 1H), 3.23 (q, J=6.6 Hz, 1H), 2.26 (d, J=4.4 Hz, 1H), 2.23 (dd, J=4.4, 2.0 Hz, 1H), 2.23 (s, 3H), 1.18 (d, J=6.6 Hz, 3H). Minor: main peaks 3.93 (d, J=12.6 Hz, 1H), 3.33 (bd, J=12.3 Hz, 1H), 2.98 (q, J=7.1 Hz, 1H), 1.25 (d, J=7.1 Hz, 3H).

The following experiments indicate anti-bacterial and anti-tumour activities and toxicity of typical Compounds (I).

Experiment 1

The following Table 4 shows anti-bacterial activity of Compounds (I) against various microorganisms expressed by the minimum growth inhibitory concentration (μg/ml) detected by the agar dilution method at pH 7.0. In this table, the microorganisms are abbreviated as follows:

SF: *Streptococcus faecium: Enterococcus faecium* ATTC 10541
SA: *Staphylococcus aureus* ATCC 6538P
PV: *Proteus vulgaris* ATCC 6897
KP: *Klebsiella pneumoniae* ATCC 10031

TABLE 4

| Compound No. (Example No) | SF | SA | PV | KP |
|---|---|---|---|---|
| 2 (2) | 1.3 | 0.63 | 1.3 | 0.16 |
| 3 (3) | 50 | 13. | 13 | 6.3 |
| 5 (5) | 1.3 | 0.31 | 0.63 | 1.3 |
| 6 (6) | 2.5 | 0.63 | 2.5 | 5.0 |
| 7 (7) | 10 | 5.0 | 10 | 2.5 |

Experiment 2

Inhibition test against the growth of HeLa $S_3$ cells

Each 0.1 ml of MEM medium containing 10% foetal calf serum and 2 mM glutamine, which contained $3 \times 10^4$ HeLa $S_3$ cells per ml, was put into each well of a 96 well microtitre plate. Without any pre-treatment, the cells were cultured overnight at a temperature of 37° C. in a $CO_2$ incubator.

On each occasion, 0.05 ml of a test sample which had been suitably diluted was added to the well. After treating with the test compound for 72 hours, the supernatant was removed. After washing once with a PBS (−), a fresh medium (0.1 ml) was added to each well, followed by incubating at a temperature of 37° C. for 2 hours in the incubator.

After removal of the supernatant, 0.1 ml of a medium containing neutral red (0.02%) was added to each well. The cells were dyed by incubating at a temperature of 37° C. for one hour in the incubator. After removal of the supernatant, followed by washing once with a physiological solution of sodium chloride, the dyestuff was removed from each sample by extraction using a mixture of 0.001N hydrochloric acid and 30% ethanol. A microplate reader was used to measure the absorption at 550 nm. By comparing the absorption of untreated cells with the absorption of the cells treated with the test compound having a pre-determined concentration, a concentration of the test compound capable of inhibiting the growth of the cells by 50% was calculated and designated as $IC_{50}$.

The results are shown in Table 5.

TABLE 5

| Compound No. | (Example No) | $IC_{50}$ (μg/ml) |
|---|---|---|
| 2 | (2) | 0.007 |
| 5 | (5) | 0.013 |
| 6 | (6) | 0.0019 |

TABLE 5-continued

| Compound No. | (Example No) | IC$_{50}$ (μg/ml) |
| --- | --- | --- |
| 7 | (7) | 0.085 |
| 10 | (10) | 0.0026 |
| 11 | (11) | 0.010 |
| 12 | (12) | 0.53 |

Experiment 3

Effect against Sarcoma 180 solid tumour and acute toxicity (1) Effect aginast Sarcoma 180 solid tumour:

$5 \times 10^6$ cells of Sarcoma 180 solid tumour cells were abdominally implanted into male mice of ddy strain. 7 days after this, ascites cells were sampled. The ascites cells were washed once with a sterilized physiological solution of sodium chloride and were used to prepare a cell suspension containing $5 \times 10^7$ cells per ml. 0.1 ml of the cell suspension was subcutaneously implanted into the right armpit of a male mouse (ddy strain; body weight $20 \pm 2$ g). 24 hours after the implantation of the tumour cells, the test compound dissolved in a physiological solution of sodium chloride containing Tween 80, was injected into the tail vein of each mouse of a group consisting of 5 animals at a dose of 0.1-0.2 ml. The anti-tumour activity of the test sample was determined as follows:

7 days after the implantation, the major axis (a) and the minor axis (b) of the tumour were measured to calculate a value of "$a \times b^2/2$" which corresponds to the volume of the tumour. The anti-tumour activity was expressed by T/C viz. the ratio of the volume of the tumours (T) of the group of animals administered with the test compound to the corresponding volume of tumours (C) of the untreated animals.

(2) Determination of ED$_{50}$:

The term ED$_{50}$ denotes the administered amount needed for reducing the volume of Sarcoma 180 solid tumours in the animals by 50% on the basis of the corresponding volume of Sarcoma 180 solid tumours in the untreated animals. On graph paper, the value T/C was indicated by an arithmetic scale on the longitudinal axis and the administered amount of test compound was indicated by a logarithmic scale on the lateral axis. A straight line indicating the relationship between the dose and T/C was determined by the the least squares method from which a dose corresponding to T/C of 0.5 was obtained.

(3) Acute toxicity:

Each animal of the test group consisting of 5 ddy mice was once administered intravenously with a test compound. After this, the animals were observed for 14 days to note the survival ratio. The LD$_{50}$ was determined by the Behrens Körber's method.

The following Table 6 shows ED$_{50}$ and LD$_{50}$ values of selected Compounds (I).

TABLe 6

| Compound No. | Example No. | ED$_{50}$ (mg/kg) | LD$_{50}$ (mg/kg) |
| --- | --- | --- | --- |
| 3 | (3) | 9.9 | 11.3 |
| 6 | (6) | 1.2 | 3.0 |
| 10 | (10) | 1.9 | 4.2 |
| 11 | (11) | 0.77 | 3.1 |

What is claimed is:

1. Mitomycin derivatives having the formula

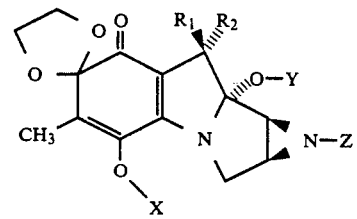

wherein
X is acyl having the structure of the formula RCO, wherein R is selected from straight or branched alkyl having 1-17 carbon atoms, alkenyl having 2-17 carbon atoms and phenyl, the alkylene chain of said alkyl being optionally interrupted by one member selected from 1-3 oxygen atoms and carbonyl;
Y is selected from hydrogen and methyl; and
Z is selected from hydrogen and methyl;
one of R$_1$ and R$_2$ represents carbamoyloxymethyl and the other represents hydrogen.

2. The Mitomycin compounds of claim 1, wherein X is acyl selected from the group consisting of acetyl, octanoyl, dodecanoyl, linoleoyl and benzoyl.

3. A mitomycin derivative according to claim 1 which is -4-acetoxy-8{methyl}-1, 1a, 2, 8, 8a, 8b-hexahydro-8a-methoxy-5-methyl-azirino pyrrolo indole-6, 7-dione 6-ethylene acetal.

4. A mitomycin derivative according to claim 1 which is -8{-methyl}-4-benzoyloxy-1, 1a, 2, 8, 8a, 8b-hexahydro-8a-methoxy-5-methyl-azirino pyrrolo indole-6, 7-dione 6-ethylene acetal.

5. A mitomycin derivative according to claim 1 which is -8{-methyl}-4-dodecanoyloxy-1, 1a, 2, 8, 8a, 8b-hexahydro-8a-methoxy-5-methyl-azirino pyrrolo indole-6, 7-dione 6-ethylene acetal.

6. A mitomycin derivative according to claim 1 which is -8{-methyl}-1, 1a, 2, 8, 8a, 8b-hexahydro-4-linoleoyloxy-8a-methoxy-5-methyl-azirino pyrrolo indole-6, 7-dione 6-ethylene acetal.

7. A mitomycin derivative according to claim 1 which is -8{-methyl}-1, 1a, 2, 8, 8a, 8b-hexahydro-8a-methoxy-5-methyl-4-octanoyloxy-azirino pyrrolo indole-6, 7-dione 6-ethylene acetal.

8. A pharmaceutical composition comprising a cytostatically or antibacterially effective amount of a mitomycin derivative according to claim 1 with a pharmacologically acceptable carrier and/or adjuvant.

9. The method for achieving cystostasis or bacteriostatis in patients which comprises the steps of administering mitomycin derivatives containing the compositions according to claim 8.

* * * * *